United States Patent
Agarkhed et al.

(10) Patent No.: US 11,607,377 B2
(45) Date of Patent: Mar. 21, 2023

(54) NON-SOAP LIQUID CLEANSER COMPOSITION COMPRISING CAPRYLIC ACID

(71) Applicant: Conopco, Inc., Trumbull, CT (US)

(72) Inventors: Ajit Manohar Agarkhed, Thane (IN); Mohini Anand Bapat, Mumbai (IN); Prem Chandar, Closter, NJ (US); Poonam Manoj Gandhi, Mumbai (IN); Anat Shiloach, Trumbull, CT (US); Guohui Wu, Woodbridge, CT (US)

(73) Assignee: CONOPCO, INC., Englewood Cliffs, NJ (US)

( * ) Notice: Subject to any disclaimer, the term of this patent is extended or adjusted under 35 U.S.C. 154(b) by 401 days.

(21) Appl. No.: 16/756,627

(22) PCT Filed: Sep. 26, 2018

(86) PCT No.: PCT/EP2018/076145
§ 371 (c)(1),
(2) Date: Apr. 16, 2020

(87) PCT Pub. No.: WO2019/081152
PCT Pub. Date: May 2, 2019

(65) Prior Publication Data
US 2020/0352836 A1   Nov. 12, 2020

(30) Foreign Application Priority Data

Oct. 17, 2017 (EP) .................................... 17198910

(51) Int. Cl.
*C11D 1/02* (2006.01)
*A61K 8/36* (2006.01)
*A61K 8/19* (2006.01)
*A61K 8/34* (2006.01)
*A61K 8/42* (2006.01)
*A61K 8/44* (2006.01)
*A61K 8/46* (2006.01)
*A61K 8/49* (2006.01)
*A61Q 17/00* (2006.01)
*A61Q 19/10* (2006.01)
*C11D 1/10* (2006.01)
*C11D 1/14* (2006.01)

(52) U.S. Cl.
CPC .............. *A61K 8/361* (2013.01); *A61K 8/19* (2013.01); *A61K 8/345* (2013.01); *A61K 8/347* (2013.01); *A61K 8/42* (2013.01); *A61K 8/44* (2013.01); *A61K 8/463* (2013.01); *A61K 8/4973* (2013.01); *A61Q 17/005* (2013.01); *A61Q 19/10* (2013.01); *C11D 1/10* (2013.01); *C11D 1/146* (2013.01); *A61K 2800/596* (2013.01); *A61K 2800/74* (2013.01)

(58) Field of Classification Search
CPC ....................................................... C11D 1/02
See application file for complete search history.

(56) References Cited

U.S. PATENT DOCUMENTS

| | | | |
|---|---|---|---|
| 5,132,037 | A | 7/1992 | Greene et al. |
| 5,681,802 | A | 10/1997 | Fujiwara et al. |
| 5,883,059 | A | 3/1999 | Furman et al. |
| 2012/0101135 | A1 | 4/2012 | Klug et al. |
| 2015/0230458 | A1 | 8/2015 | Winters et al. |
| 2017/0174912 | A1* | 6/2017 | Bons .................... C09D 9/04 |
| 2017/0247644 | A1* | 8/2017 | Li ....................... C07C 309/58 |

FOREIGN PATENT DOCUMENTS

| | | |
|---|---|---|
| CN | 102267895 | 12/2011 |
| CN | 106038348 | 10/2016 |
| CN | 106232091 | 12/2016 |
| EP | 0044582 | 1/1982 |
| JP | H10500962 | 1/1998 |
| JP | 2002145719 | 5/2002 |
| JP | 2002540898 | 12/2002 |
| JP | 2016026197 | 2/2016 |
| WO | WO9532705 | 12/1995 |
| WO | WO0061107 | 10/2000 |

OTHER PUBLICATIONS

IPRP2 in PCTEP2018076145; Feb. 12, 2020.
Internet Citation; Fatty Acids Composition of Virgin Coconut Oil; Mar. 16, 2012; p. 1-1.
Frederic Pilz; SOFW Journal; Sorbitan Caprylate—A New Preservative fo Formulations; Aug. 1, 2012; pp. 32-35.
S.A. Kim et al.; International Journal of Antimicrobial Agents; Antibacterial activity of caprylic acid for potential application as an active antiseptic ingredient in consumer antiseptics; Sep. 29, 2016; pp. 765-767; XP029836401; vol. 48/Issue 6.
Search Report and Written Opinion in PCTEP2018076145; dated Nov. 22, 2018.
Search Report and Written Opinion in EP17198910; dated May 4, 2018.
Written Opinion 2 in PCTEP2018076145; dated Oct. 2, 2019.
Georgieva et al.; "Synergistic Growth of Giant Wormlike Micelles in Ternary Mixed Surfactant Solutions: Effect of Octanoic Acid", Langmuir 32, 2016 American Chemical Society, pp. 12885-12893.
Mitrinova et al.; "Efficient control of the Rheological and Surface Properties of Surfactant Solutions Containing C8-C18 Fatty Acids as Cosurfactants", Langmuir 29, 2013 American Chemical Society, pp. 8255-8265.
Zhuang Mengu et al.; Study on the antiseptic synergistic effect of sorbitan caprylate in personal care products; China Detergent Industry; Jun. 15, 2017; pp. 39-43, with english translation; No. 6; China.

\* cited by examiner

*Primary Examiner* — Charles I Boyer
(74) *Attorney, Agent, or Firm* — Krista A. Kostiew

(57) ABSTRACT

This invention relates to syndet-based compositions having pH of 4.5 to 5.5 wherein use of caprylic acid has been unexpectedly found to enhance bacterial kill.

14 Claims, No Drawings

NON-SOAP LIQUID CLEANSER COMPOSITION COMPRISING CAPRYLIC ACID

CROSS REFERENCE TO RELATED APPLICATIONS

The present application is a U.S. National Phase Application under 35 U.S.C. § 371 of International Application No. PCT/EP2018/076145, filed on Sep. 26, 2018, which claims priority to European Patent Application No. 17198910.6, filed on Oct. 27, 2017, the contents of which are incorporated herein in their entireties.

FIELD OF THE INVENTION

The present invention relates to non-soap (sometimes referred to as syndet or synthetic detergent) based liquid cleansers having enhanced anti-bacterial activity. Specifically, it has been found that the addition of caprylic acid (octanoic acid) to mild pH (pH of 4.5 to 5.5, preferably 4.5 to 5.1, especially 4.5 to 4.9) liquid syndet composition surprisingly enhances antibacterial activity at this pH range.

BACKGROUND OF THE INVENTION

Personal cleansing products, including liquids, play an important role in hygiene.

Hygiene is typically delivered through the use of antibacterial agents, such as phenolic antimicrobial compounds (e.g. triclosan, triclocarbon, PCMX), non-phenolic antimicrobial compounds (e.g., quaternary ammonium salts), and chemicals with free metal ions (e.g. $Ag^+$, $Zn^{2+}$, $Cu^{2+}$).

However, in compositions which are in a mild pH range (e.g., 4.5 to 5.5, or 4.5 to 5.1, particularly 4.5 to 5.0 or 4.5 to 4.9; products with pH lower than 4.5 are generally considered harsh and capable of causing some harm to the skin), it is difficult to provide enhanced antibacterial activity, especially if one wishes to avoid use of the antibacterial agents. For example, there has been concern relating to the use of antibacterial agents, their potential effect on the environment, and their potential role in promoting drug resistance. The antibacterial agents are facing increasing scrutiny from regulatory agencies, not to mention the added material handling and costs during the production process. Thus, it would be greatly beneficial to provide antibacterial effect without use of traditional antibacterial agents.

In addition, it is difficult to achieve broad effect against both gram positive and gram negative bacteria; and it is difficult to achieve quick effect (effect in 20 seconds or less, especially 10 seconds or less).

In synthetic surfactant based liquid cleansers (especially those based on 50% or more anionics such as alkyl sulfates), for example, it has now been found that addition of $C_8$ fatty acid can provide fast, broad-based antibacterial effect at pH ranges of 4.5 to 5.5, preferably 4.5 to 5.1, particularly 4.5 to 4.9. While traditional antibacterial agents such as those noted above can slightly improve the effect of $C_8$ fatty acid alone, significant improvement is seen even in compositions without traditional antibacterial agent.

The effect of caprylic acid (also known as octanoic acid) alone (again, even assuming absence of traditional antibacterial agents) can be further strengthened when the caprylic acid is combined with certain organic acids (e.g., phenylpropionic acid).

The effect can also be further enhanced when caprylic acid is combined with other organic acids having pKa greater than 4.0 but less than 5.0 (e.g., benzoic acid, sorbic acid and other organic acids defined herein). Phenylpropionic acid, noted just above, works particularly well with caprylic acid in terms of efficacy. It has pKa>4.5; and also has both a relatively high Log P (partition coefficient between aqueous and lipophilic phases, usually measured using octanol and water) and high solubility in water. These parameters ensure that the availability of organic acid is relatively high at pH 4.5 to about 4.9 (due to its high pKa and water solubility), and is at the same time hydrophobic enough to partition into bacteria membrane. Moreover, the effect can be enhanced when combined with certain non-ionic molecules defined herein.

In a 2013 article to Mitrinova et al. ("Efficient control of the Rheological and Surface Properties of Surfactant Solutions Containing $C_8$ to $C_{18}$ Fatty Acids as Co-surfactants", published Jun. 11, 2013 in Langmuir, there are disclosed compositions comprising sodium lauroyl ether sulfate (SLES) and cocoamidopropyl betaine (CAPB) surfactant systems and further comprising $C_8$ to $C_{18}$ fatty acids; the reference describes desirable effects of these fatty acids on rheology of the surfactants. There is nothing recognizing more specifically the use of $C_8$ in such systems and their effect on antibacterial efficacy particularly in compositions of specific mild pH range. There is no specific discussion of pH and antibacterial effect at certain pH ranges.

In a 2016 article by Georgieva et al. ("Synergistic Growth of Giant Wormlike Micelles in Ternary Mixed Surfactant Solutions: Effect of Octanoic Acid", published 2016 in Langmuir, it is noted that minimal pH of a SLES/CAPB/caprylic acid system is about 5.1. Lower pH and/or antibacterial effectiveness are not noted.

EP 044 582 to P&G discloses compositions in which a specific combination of free fatty acids and fatty alkylolamide in a ratio of 1:3 to 3:1 is used as lather booster for anionic surfactant. Although coconut oil fatty acid is disclosed at level of 0.2% by wt. (Example 1), it is known that caprylic acid comprises no more than about 10% of coconut oil (see for example fatty acid composition of Virgin Coconut Oil at http://www.thevirgincoconutoil.com/articleitem-.php?articleid=163. Thus, the coconut oil blend comprises no more than 0.2% caprylic.

SUMMARY OF THE INVENTION

The present invention relates to non-soap (i.e., synthetic surfactant based) liquid compositions. In particular, it relates to use of caprylic acid in mild pH (e.g., pH 4.5 to 5.5, preferably 4.5 to 5.1, especially 4.5 to 5.0 or 4.5 to 4.9) liquids. Preferably, the caprylic acid is used to boost the antimicrobial efficacy against both gram negative and gram positive bacteria in the absence of other antibacterial (AB) agents.

More particularly, the invention comprises:
1) 5 to 25% by wt., preferably 8 to 20% of an anionic surfactant (e.g, alkyl sulfate such as sodium lauryl ether sulfate, SLES; or amino acid based surfactant such as glutamate or glycinate, as well as taurates); the cleansers can be used for germ removal applications such as hand wash liquids or foamers.
    Low-surfactant formulations especially work well, where the preferred surfactant levels are 5 to 8%, preferably 6.0 to 7.5% by wt.; The availability of caprylic acid is optimal at low surfactants due to less partition into micelles. Example 7 and 8 are examples of cleanser compositions with high foaming properties containing relatively lower surfactants.

The non-soap cleansers are particularly suited for applications like liquid hand soap, foaming liquid hand soap, liquid body wash, bath gel, exfoliating cleanser, shampoo, cleaning wipe, or industrial soap. The formulations can be used or as a base of a soap composition to prevent and treat a variety of microbial infections by cleansing or treating the skin and/or hair (fur) of a subject in need thereof.

2) Optional non-ionic surfactant (e.g., 0 to 5%, preferably 0.5 to 4% by wt.), preferably an alkylamide alkanolamine (e.g., alkanolamide such as cocomonoethanolamide);

3) Optional amphoteric and/or zwitterionic surfactant (although amido betaines are preferably minimized, (e.g., 2% by wt. or less, preferably 1% by wt., more preferably 0.01 to 0.5%) or preferably absent altogether); the presence of amido betaines suppress the boosting effect of caprylic acid in terms of the formulations' antimicrobial efficacy (see Example 4 versus Example 2 in Examples)

4) 0.5 to 3%, especially 1.0 to 3% and especially 1.1 or 1.2 or 1.3 to 3% caprylic acid, wherein pH of the composition is 4.5 to 5.5, preferably 4.5 to 5.1, more preferably 4.5 to 5.0 or 4.5 to 4.9.

Unexpectedly, it has been found that caprylic acid when used at certain minimum levels boosts broad spectrum antibacterial activity (e.g., against both gram positive and gram negative bacteria); although small amounts of traditional antibacterial actives can slightly boost activity of $C_8$ as active, the $C_8$ is highly effective even in the absence of antibacterial actives; such antibacterial actives are optional in formulations and are typically present at levels of 0 to 0.4%, preferably 0 to 0.2%, more preferably 0.1 to 0.2%.

Examples of antibacterial actives which may be used include actives such as silver, phenoxyethanol and mixtures thereof. Other actives include thymol, terpineol and mixtures; the latter may of course be used alone (or as mixtures of thymol and terpineol); or in combination with silver, phenoxyethanol or other known antibacterials or mixtures of such known antibacterials.

In one form, when caprylic acid is further combined with certain organic acids which have a pKa between 4.0 and 5.0, log P greater than 0, and water solubility greater than 0.014 g/100 ml (e.g., benzoic acid, sorbic acid, decanoic acid, adipic acid, hydroxybenzoic acid, and the like and/or mixtures of any of these), antibacterial efficacy of caprylic acid is further enhanced. (see Examples 9 to 12).

In another form, when caprylic acid is further combined with organic acid with pKa between 4.5 and 5.0, relatively high log P (log P>1.8) as well as relatively high water solubility (solubility>0.5 g/100 ml), an example of such organic acid being phenylpropanoid (e.g., phenylproponoic acid), the antibacterial effect is even stronger (see Example 13.)

In another form, combination of caprylic acid with certain non-ionic molecules (e.g., capryl glycol, phenoxyethanol, sorbitan caprylate, and mixtures), activity of caprylic is enhanced even further (see Example 15 and 16).

The invention further provides a process for making the compositions of the invention by providing ingredients in the amounts specified in the description of the composition, combining these, and packaging the resulting mixture in a container.

The invention further relates to use of 0.5 to 30% caprylic acid in composition comprising 5 to 25% by wt. anionic surfactant, 0 to 5%, preferably 0.5 to 4% by wt. non-ionic surfactant and optional amphoteric surfactants, where pH of composition is 4.5 to 5.5, to provide antibacterial activity against both gram positive and gram negative bacteria.

DETAILED DESCRIPTION OF THE INVENTION

Except in the examples, or where otherwise explicitly indicated, all numbers in this description indicating amounts of material or conditions of reaction, physical properties of materials and/or use are to be understood as modified by the word "about."

As used throughout, ranges are used as shorthand for describing each and every value that is within the range. Any value within the range can be selected as terminus of the range. The use of and/or indicates that any one from the list can be chosen individually, or any combination from the list can be chosen.

For the avoidance of doubt, the word "comprising" is intended to mean "including" but not necessarily "consisting of" or "composed of." In other words, the listed steps or options need not be exhaustive.

Unless indicated otherwise, all percentages for amount or amounts of ingredients used are to be understood to be percentages by weight based on the active weight of the material in the total weight of the composition, which total is 100%.

The present invention relates to synthetic based liquid (wherein anionic comprises 50% or more of the surfactant system) which comprises mild pH. Use of caprylic acid has been unexpectedly found to enhance AB activity, even in the absence of other antibacterial agents.

Specifically, the composition comprises:
1) 5 to 25% by wt., preferably 8 to 20% by wt. of anionic (which is 50% or more of surfactant system); in one aspect, e.g., the composition can be used for germ removal applications such as hand wash liquid or foamers. Low-surfactant formulations especially work well, where the preferred surfactant levels are 5 to 8%, preferably 6.0 to 7.5% by wt.; The availability of caprylic acid is optimal at low surfactants due to less partition into micelles.
2) Optional non-ionic surfactant (e.g., 0 to 5%, preferably 0.5 to 4% by wt.), particularly alkylamide alkanolamine;
3) optional amphoteric and/or zwitterionic surfactant (amido betaines are preferably minimized);
4) 0.5 to 3%, especially 1.0 to 3%, and especially 1.1 or 1.2 or 1.3 to 3% by wt. caprylic acid; and
5) optional antibacterial actives;
wherein pH is 4.5 to 5.5, preferably 4.5 to 5.1, preferably 4.5 to 5.0 or 4.5 to 4.9.

The anionic surfactant may be, for example, an aliphatic sulfonate, such as a primary alkane (e.g., $C_8$-$C_{22}$) sulfonate, primary alkane (e.g., $C_5$-$C_{22}$) disulfonate, $C_8$-$C_{22}$ alkene sulfonate, $C_8$-$C_{22}$ hydroxyalkane sulfonate or alkyl glyceryl ether sulfonate (AGS); or an aromatic sulfonate such as alkyl benzene sulfonate.

The anionic may also be an alkyl sulfate (e.g., $C_{12}$-$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alky or alkenyl having 8 to 18 carbons, preferably 12 to 18 carbons, n has an average value of greater than 1.0, preferably between 2 and 3; and M is a solubilizing cation such as sodium, potassium, ammonium or substituted ammonium. Ammonium and sodium lauryl ether sulfates are preferred.

Particularly preferred is alkali metal lauryl ether sulfate (such as sodium lauryl ether sulfate).

The anionic may also be alkyl sulfosuccinates (including mono- and dialkyl, e.g., $C_6$-$C_{22}$ sulfosuccinates); alkyl and acyl taurates, alkyl and acyl sarcosinates, sulfoacetates, $C_8$-$C_{22}$ alkyl phosphates and phosphates, alkyl phosphate esters and alkoxyl alkyl phosphate esters, acyl lactates, $C_8$-$C_{22}$ monoalkyl succinates and maleates, sulphoacetates, and acyl isethionates.

Sarcosinates are generally indicated by the formula $RCON(CH_3)CH_2CO_2M$, wherein R ranges from $C_8$ to $C_{20}$ alkyl and M is a solubilizing cation.

Taurates are generally identified by formula:

wherein $R^2$ ranges from $C_8$-$C_{20}$ alkyl, $R^3$ ranges from $C_2$-$C_4$ alkyl and M is a solubilizing cation.

Another class of anionics are carboxylates such as follows:

wherein R is $C_8$ to $C_{20}$ alkyl; n is 0 to 20; and M is as defined above.

Another carboxylate which can be used is amido alkyl polypeptide carboxylates such as, for example, Monteine LCQ® by Seppic.

Another surfactant which may be used are the $C_8$-$C_{18}$ acyl isethionates. These esters are prepared by reaction between alkali metal isethionate with mixed aliphatic fatty acids having from 6 to 18 carbons atoms and an iodine value of less than 20. At least 75% of the mixed fatty acids have from 12 to 18 carbon atoms and up to 25% have from 6 to 10 carbon atoms.

The anionic may preferably be an amino acid based anionic such as glutamate or glycinate.

The non-ionic which may be used includes the reaction products of compounds having a hydrophobic group and a reactive hydrogen atom, for example aliphatic alcohols, acids, amides or alkyl phenols with alkylene oxides, especially ethylene oxide either alone or with propylene oxide. Specific non-ionic detergent compounds are alkyl ($C_6$-$C_{22}$) phenols-ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ehtylenediamine. Other so-called nonionic detergent compounds include long chain tertiary amine oxides, long chain tertiary phosphine oxides and dialkyl sulphoxides.

The non-ionic surfactant may also be a sugar amide, such as a polysaccharide amide.

A particularly preferred non-ionic is alkylamide alkanolamine (e.g., cocomonoethanolamide or CMEA). Preferably, CMEA is used in around 0.5 to 2% by wt.

Zwitterionic surfactants (optional) are exemplified by those which can be broadly described as derivatives of aliphatic quaternary ammonium, phosphonium, and sulfonium compounds, in which the aliphatic radicals can be straight or branched chain, and where one of the aliphatic substituents contains from about 8 to 18 carbon atoms and one contains an anionic group, e.g., carboxy, sulfonate, sulfate, phosphate, or phosphonate. A general formula for these compounds is:

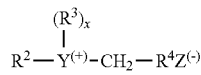

wherein $R^2$ contains an alkyl, alkenyl, or hydroxyl alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate sulfonate, sulfate, phosphonate, and phosphate groups.

Amphoteric detergents which may be used in this invention (optional) include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

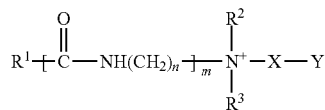

where $R^1$ is alkyl or alkenyl of 7 to 18 carbon atoms;
$R^2$ and $R^3$ are each independently alkyl, hydroxyalkyl or carboxyalkyl of 1 to 3 carbon atoms;
N is 2 to 4;
M is 0 to 1;
X is alkylene of 1 to 3 carbon atoms optionally substituted with hydroxyl, and
Y is $—CO_2—$ or $—SO_3—$ Amphoteric detergents within the above general formula include simple betaines of formula:

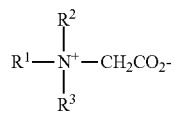

and amido betaines of formula:

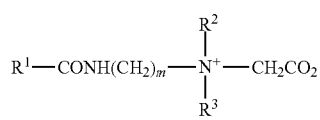

where m is 2 or 3.

It is preferred that amido betaines be minimized or be absent altogether.

As indicated, compositions should comprise 0.1 to 5%, preferably 0.5 to 3% caprylic acid (octanoic acid).

pH of compositions should be 4.5 to 5.5, preferably 4.5 to 5.1, more preferably 4.5 to 5.0 or 4.5 to 4.9 pH levels of 4.5 to 4.9 are particularly preferred.

In one aspect, when caprylic acid is further combined with certain organic acids which have a pKa between 4.0 and 5.0, log P greater than 0, and water solubility greater than 0.014 g/100 ml (e.g., benzoic acid, sorbic acid, decanoic acid, adipic acid, hydroxybenzoic acid, and the like and/or mixtures of any of these), antibacterial efficacy of caprylic acid is enhanced.

In another aspect, when caprylic acid is further combined with organic acid with pKa between 4.5 and 5.0, relatively high log P (log P>1.8) as well as relatively high water solubility (solubility>0.5 g/100 ml), such as a phenylpropanoid (e.g., phenylproponoic acid), the antibacterial effect is even stronger (see Example 13).

In another aspect, combination of caprylic acid with certain non-ionic molecules (e.g., capryl glycol, phenoxyethanol, sorbitan caprylate, and mixtures), activity of caprylic acid is enhanced even further (see Example 15 and 16).

Antibacterial actives may also further optionally be added to the compositions. These may include thymol, terpineol, silver, phenoxyethanol and mixtures thereof. As noted, $C_8$ is highly effective, even in the absence of such antibacterial agents.

The invention further provides a process for making the compositions of the invention by providing ingredients in the amounts specified in the description of the composition, combining these, and packaging the resulting mixture in a container.

The invention further relates to use of 0.5 to 30% caprylic acid in composition comprising 5 to 25% by wt. anionic surfactant, 0 to 5%, preferably 0.5 to 4% by wt. non-ionic surfactant and optional amphoteric surfactants where pH of composition is 4.5 to 5.5 to provide antibacterial activity against both gram positive and gram negative bacteria.

Examples

The following non-limiting examples are provided to further illustrate the invention; the invention is not in any way limited thereto. The following protocol was used to evaluate biocidal activity.

In-Vitro Time-Kill Protocol
Soap Solution Preparation

Solution preparation depends, in part, on the particular form of the liquid soap formulation. For example, formulations that are not diluted in use, e.g., self-foaming formulations, are employed as is. A formulation that contains 30 wt. % or less of detersive surfactant and which is intended to be diluted in use is mixed with water to form a soap solution containing 62.5 wt % of the initial formulation. A formulation that contains more than 30 wt. % of detersive surfactant and which is intended to be diluted in use is mixed with water to form a soap solution containing 16 wt % of the initial formulation.

Bacteria

*E. coli* ATCC 10536 and *Staphylococcus aureus* ATCC 6538, were used in this study to represent Gram negative and Gram positive bacteria, respectively. The bacteria were stored at −80° C. Fresh isolates were cultured twice on Tryptic Soy Agar plates for 24 hours at 37° C. before each experiment.

In-Vitro Time-Kill Assay

Time-kill assays were performed according to the European Standard, EN 1040:2005 entitled "Chemical Disinfectants and Antiseptics—Quantitative Suspension Test for the Evaluation of Basic Bactericidal Activity of Chemical Disinfectants and Antiseptics—Test Method and Requirements (Phase 1)" incorporated herein by reference. Following this procedure, growth-phase bacterial cultures at $1.5 \times 10^8$ to $5 \times 10^8$ colony forming units per ml (cfu/ml) were treated with the soap solutions (prepared as described above) at 25° C. In forming the test sample 8 parts by weight of the soap solution, prepared as described above, were combined with 1 part by weight of culture and 1 part by weight of water. After 10, 20, and 30 seconds of exposure, samples were neutralized to arrest the antibacterial activity of the soap solutions. Then test solutions were serially diluted, plated on solid medium, incubated for 24 hours and surviving cells were enumerated. Bactericidal activity is defined as the log reduction in cfu/ml relative to the bacterial concentration at 0 seconds. Cultures not exposed to any soap solutions serve as no-treatment controls.

The $\log_{10}$ reduction was calculated using the formula:

$$\text{Log}_{10} \text{ Reduction} = \log_{10} (\text{numbers control}) - \log_{10} (\text{test sample survivors})$$

Examples

Below in Table 1 are found a control example and Examples 1 to 4 of the invention.

TABLE 1

| Ingredient (wt %) | Raw ingredient purity | Control | Example 1 | Example 2 | Example 3 | Example 4 |
|---|---|---|---|---|---|---|
| Water | 100% | Balance to 100 | Balance to 100 | Balance to 100 | Balance to 100 | Balance to 100 |
| Ethylene Diamine Tetra acetic acid, tetra sodium salt | 39% | 0.1 | 0.1 | 0.1 | 0.1 | 0.1 |
| Acrylate copolymers | 30% | 2 | 2 | 2 | 2 | 2 |
| Cocomonoethanolamide | 100% | 1 | 1 | 1 | 1 | 1 |
| SLES | 70% | 16 | 16 | 16 | 16 | 16 |
| EGDS | 100% | 1 | 1 | 1 | 1 | 1 |
| Caprylic acid C8 | 99% | 0.0 | 1.0 | 1.5 | 2.0 | 1.5 |
| Cocoamidopropylbetaine | 30% | 0.0 | 0.0 | 0.0 | 0.0 | 3.0 |
| Glycerine | 100% | 2 | 2 | 2 | 2 | 2 |
| Dimethylol dimethyl hydantoin (DMDM) | 55% | 0.4 | 0.4 | 0.4 | 0.4 | 0.4 |

TABLE 1-continued

| Ingredient (wt %) | Raw ingredient purity | Control | Example 1 | Example 2 | Example 3 | Example 4 |
|---|---|---|---|---|---|---|
| NaCl | 90% | 1 | 1 | 1 | 1 | 1 |
| pH (adjusted with NaOH and Citric Acid) | | 4.9 | 4.9 | 4.5 | 4.7 | 4.7 |

TABLE 2

| | Biocidal Activity | | | | | |
|---|---|---|---|---|---|---|
| | Log10 Reduction against *e. coli* ATCC 10536 | | | Log10 Reduction against *s. aureus* ATCC 6538 | | |
| | 10 Seconds | 20 Seconds | 30 Seconds | 10 Seconds | 20 Seconds | 30 Seconds |
| Control | −0.1 | −0.1 | −0.1 | 0.1 | 0.2 | 0.4 |
| Example 1 | 0.8 | 1.0 | 1.2 | / | / | / |
| Example 2 | 1.8 | >4.2 | >4.2 | 1.6 | 3.1 | 3.5 |
| Example 3 | 3.8 | >4.0 | >4.0 | / | / | / |
| Example 4 | 0.9 | 3.3 | >4.2 | 0.5 | 1.8 | 2.2 |

As demonstrated by the Table 2 data, at the indicated contact times, addition of caprylic acid at 1.0%, 1.5%, and 2.0% (Example 1, 2, 3, 4) boost the antimicrobial efficacy compared to the control. Adding cocoamidopropyl betaine is still effective relative to the control, but suppresses the boosting effect relative to example with same amount of caprylic acid; as seen, Example 4 has relatively less antimicrobial efficacy than Example 2.

Examples 2, 3 and 4 versus Example 1 also shows that use of greater than 1.0% caprylic acid (e.g., 1.1 or 1.2 or 1.5 to 3%) is particularly effective.

TABLE 3

| Ingredient (wt %) | Example 5 | Example 6 |
|---|---|---|
| Water | Balance to 100 | Balance to 100 |
| Ethylene diamine tetra acetic acid, tetra sodium salt | 0.1 | 0.1 |
| Sodium lauryl ether sulfate (SLES) | 7 | 7 |
| Cocaminoethanolamide (CMEA) | 1 | 1 |
| Caprylic acid C8 | 1 | 1 |
| Benzoic acid | 1 | 1 |
| Methylchloroisothiozolinone | 0.06 | 0.06 |
| Benzophenone-4 | 0.1 | 0.1 |
| Propylene glycol | 6 | 6 |
| NaOH | To adjust pH | To adjust pH |
| pH | 4.9 | 5.4 |

TABLE 4

| | Biocidal Activity Log₁₀ Reduction against *e. coli* ATCC 10536 | | |
|---|---|---|---|
| | Contact Time | | |
| | 10 Seconds | 20 Seconds | 30 Seconds |
| Example 5 pH 4.9 | 1.1 | 3.1 | >3.4 |
| Example 6 pH 5.4 | 0.8 | 1.4 | 2.8 |

As demonstrated by the Table 4 data, at the indicated contact times, Example 5 at pH 4.9 had greater bactericidal efficacy against *E. coli* ATCC 10536 than Example 6 at pH 5.4; this demonstrates the particularly strong effect of pH in the range 4.5 to 5.1, or especially 4.5 to 5.0, especially 4.5 to 4.9, in relation to the antimicrobial efficacy of non-soap formulations containing caprylic acid.

Examples 7 and 8 are directed to the cleanser formulations with high foaming properties with caprylic acid. At relatively lower surfactant level at about 5% to 8% in these particular examples, caprylic acid works especially well due to increased availability.

TABLE 5

| Ingredient (wt %) | Example 7 | Example 8 |
|---|---|---|
| Water | Balance to 100 | Balance to 100 |
| Ethylene diamine tetra acetic acid, tetra sodium salt | 0.1 | 0.1 |
| SLES | 7 | 5.5 |
| CMEA | 1 | 0.5 |
| Caprylic acid C8 | 1 | 0.75 |
| Benzoic acid | 1.5 | 0.75 |
| Methylchloroisothiozolinone | 0.06 | 0.06 |
| Benzophenone-4 | 0.1 | 0.1 |
| Propylene glycol | 6 | / |
| PEG 200 | / | 6 |
| NaOH | To adjust pH | To adjust pH |
| pH | 4.53 | 4.9 |

TABLE 6

Biocidal Activity
Log₁₀ Reduction against *e. coli* ATCC 10536

| | Log10 Reduction against *e. coli* ATCC 10536 | | | Log10 Reduction against *s. aureus* ATCC 6538 | | |
|---|---|---|---|---|---|---|
| | 10 Seconds | 20 Seconds | 30 Seconds | 10 Seconds | 20 Seconds | 30 Seconds |
| Control | −0.1 | −0.1 | −0.1 | 0.1 | 0.2 | 0.4 |
| Example 7 | 3.5 | >3.5 | >3.5 | | Not measured | |
| Example 8 | >3.8 | >3.8 | >3.8 | 3.5 | >3.8 | >3.8 |

As demonstrated by the Table 6 data, at the indicated contact times, Examples 7 and 8 had greater bactericidal efficacy against both *E. coli* ATCC 10536 and *S. aureus* ATCC 6538 than control (no Caprylic Acid).

TABLE 7

Physical properties of various organic acids

| Organic acids | pKa | LogP | Solubility in water |
|---|---|---|---|
| Tartaric acid | 3.22, 4.85 | −1.43 | 133 g/100 ml |
| Caprylic Acid | 4.89 | 3.05 | 0.068 g/100 ml |
| Benzoic acid | 4.19 | 1.87 | 0.344 g/100 ml (25° C.) |
| Adipic acid | 4.43, 5.41 | 0.08 | 2.4 g/100 ml (25° C.) |
| Hydroxybenzoic acid | 4.54 | 1.58 | 0.5/100 ml |
| Sorbic acid | 4.76 | 1.47 | 0.16/100 ml (20° C.) |
| Decanoic acid | 4.9 | 4.09 | 0.015 g/100 ml (20° C.) |
| 3-Phenylpropionic acid | 4.65 | 1.84 | 0.59 g/100 ml |

TABLE 9

Biocidal Activity
Log₁₀ Reduction against *e. coli* ATCC 10536

| | Organic acids | Log10 Reduction against *e. coli* ATCC 10536 | | |
|---|---|---|---|---|
| | | 10 Seconds | 20 Seconds | 30 Seconds |
| Example 1 | 1% Caprylic acid | 0.8 | 1.0 | 1.2 |
| Comparative C | 1% Caprylic acid + 2% Tartaric acid | −0.8 | 0.3 | 0.3 |
| Example 9 | 1% Caprylic acid + 2% Benzoic acid | 1.2 | 2.9 | 3.0 |
| Example 10 | 1% Caprylic acid + 2% Adipic acid | 1.0 | 3.0 | 3.4 |
| Example 11 | 1% Caprylic acid + 2% Hydroxybenzoic acid | 0.9 | 3.1 | 3.5 |
| Example 12 | 1% Caprylic acid + 2% Sorbic acid | 1.0 | 2.4 | 3.0 |

TABLE 8

| Ingredient (wt %) | Raw ingredient purity | Comparative C | Example 9 | Example 10 | Example 11 | Example 12 | Example 13 |
|---|---|---|---|---|---|---|---|
| Water | 100% | Balance to 100 | Balance to 100 | Balance to 100 | Balance to 100 | Balance to 100 | Balance to 100 |
| Ethylene Diamine Tetra acetic acid, tetra sodium salt | 39% | 0.1 | 0.1 | 0.1 | 0.1 | 0.1 | 0.1 |
| Acrylate copolymers | 30% | 2 | 2 | 2 | 2 | 2 | 2 |
| NaOH | 47% | To adjust pH | To adjust pH | To adjust pH | To adjust pH | To adjust pH | To adjust pH |
| Cocomonoethanolamide | 100% | 1 | 1 | 1 | 1 | 1 | 1 |
| SLES | 70% | 16 | 16 | 16 | 16 | 16 | 16 |
| Ethylene glycol distearate (EGDS) | 100% | 1 | 1 | 1 | 1 | 1 | 1 |
| Caprylic acid C8 | 99% | 0.0 | 1.0 | 1.0 | 1.0 | 1.0 | 1.0 |
| Tartaric acid | 30% | 2.0 | / | / | / | / | / |
| Benzoic acid | 100% | / | 2.0 | / | / | / | / |
| Adipic acid | 100% | / | / | 2.0 | / | / | / |
| hydroxybenzoic acid | 100% | / | / | / | 2.0 | / | / |
| Sorbic acid | 100% | / | / | / | / | 2.0 | / |
| 3-Phenylpropionic acid | 100% | / | / | / | / | / | 2.0 |
| Glycerine | 100% | 2 | 2 | 2 | 2 | 2 | 2 |
| DMDM hydantoin (Glydant 2000) | 55% | 0.4 | 0.4 | 0.4 | 0.4 | 0.4 | 0.4 |
| Citric acid (for pH adjustment) | 90% | To adjust pH | To adjust pH | To adjust pH | To adjust pH | To adjust pH | To adjust pH |
| NaCl | 90% | 1 | 1 | 1 | 1 | 1 | 1 |

TABLE 9-continued

Biocidal Activity
Log₁₀ Reduction against *e. coli* ATCC 10536

| | Organic acids | Log10 Reduction against *e. coli* ATCC 10536 | | |
|---|---|---|---|---|
| | | 10 Seconds | 20 Seconds | 30 Seconds |
| Example 13 | 1% Caprylic acid + 2% 3-Phenylpropionic acid | 1.2 | 3.2 | 3.6 |

As demonstrated by the Table 9 data, at the indicated contact times, Examples 9 to 13 (combination of Caprylic acid and organic acids which satisfy requirements that pKa is between 4.0 and 5.0, log P>0, and water solubility>0.014 g/100 ml) had greater bactericidal efficacy against *E. coli* ATCC 10536 than Example 1 (containing only caprylic acid). Comparative C is a negative example of organic acid which has too low log P.

TABLE 10

| Ingredient | | Comparative D | Example 15 | Comparative E | Example 16 |
|---|---|---|---|---|---|
| Water | | Balance to 100 | Balance to 100 | Balance to 100 | Balance to 100 |
| Ethylene Diamine Tetra acetic acid, tetra sodium salt | 39% | 0.1 | 0.1 | 0.1 | 0.1 |
| Acrylate copolymers | 30% | 2 | 2 | 2 | 2 |
| NaOH | 47% | To adjust pH | To adjust pH | To adjust pH | To adjust pH |
| Cocomonoethanolamide | 100% | 1 | 1 | 1 | 1 |
| SLES | 70% | 16 | 16 | 16 | 16 |
| EGDS | 100% | 1 | 1 | 1 | 1 |
| Caprylyl Glycol | 100% | 0 | 0 | 0 | 1 |
| Sorbitan Caprylate | 100% | 0 | 2 | 0 | 0 |
| Caprylic acid C8 | 99% | 2 | 2 | 1 | 1 |
| Glycerine | 100% | 2 | 2 | 2 | 2 |
| DMDM hydantoin (Glydant 2000) | 55% | 0.4 | 0.4 | 0.4 | 0.4 |
| Citric acid (for pH adjustment) | 90% | To adjust pH | To adjust pH | To adjust pH | To adjust pH |
| NaCl | 90% | 1 | 1 | 1 | 1 |
| pH | | 4.78 | 4.78 | 4.78 | 4.78 |
| viscosity cps | | 1600 | 1600 | 1600 | 1600 |

TABLE 11

Biocidal Activity

| | Non-ionics | Difference of Log10 Reduction against *e. coli* ATCC 10536 | | |
|---|---|---|---|---|
| | | 10 Seconds | 20 Seconds | 30 Seconds |
| Example 15 vs. Comparative D | 2% caprylic acid + 2% sorbitan caprylate | 0.0 | 0.3 | 1.4 |
| Example 16 vs. Comparative E | 1% caprylic acid + 1% caprylyl glycol | 0.2 | 0.9 | >0.4 |

As demonstrated by the Table 11 data, at the indicated contact times, Examples 15 and 16 (caprylic acid combined with non-ionics, such as sorbitan caprylate or caprylyl glycol) had greater bactericidal efficacy than their corresponding Comparatives D and E (caprylic acid alone with no non-ionics).

The invention claimed is:

1. A liquid composition comprising:
    a) 5 to 25% anionic surfactant;
    b) 0 to 5% non-ionic surfactant
    c) optional amphoteric surfactant,
    wherein the anionic surfactant is 50% or more of surfactants;
    d) 0.5 to 3% caprylic acid;
    wherein a pH is 4.5 to 5.5,
    wherein there is additionally present an organic acid having a pKa 4.5 to 5.0, a log P greater than 1.8 and water solubility greater than 0.5 g/100 ml;
    wherein the organic acid is phenylpropanoic acid.

2. The liquid composition according to claim 1, wherein the anionic surfactant is alkyl sulfate, amino-acid based surfactant or mixtures thereof.

3. The liquid composition according to claim 1, wherein the non-ionic surfactant is present at a level of 0.5 to 4%.

4. The liquid composition according to claim 1, wherein the non-ionic surfactant, if present, is cocomonoalkanolamide.

5. The liquid composition according to claim 1, which additionally comprises antibacterial agents.

6. The liquid composition according to claim 5, wherein such antibacterial agent is selected from the group consisting of thymol, terpineol, silver, phenoxyethanol, and mixtures thereof.

7. The liquid composition according to claim 1, wherein the organic acid is 3-phenylpropionic acid.

8. The liquid composition according to claim 1, wherein there is additionally present a non-ionic molecule, separate from the non-ionic surfactant.

9. The liquid composition according to claim 8, wherein the non-ionic molecule is selected from the group consisting of capryl glycol, phenoxyethanol, sorbitan caprylate, and mixtures thereof.

10. The liquid composition according to claim 1, wherein total surfactant is present at 5 to 8% of the composition.

11. A process of making the compositions of claim 1, comprising:
    a) providing 5 to 25% by wt. anionic surfactant, 0 to 5%, non-ionic surfactant, optional amphoteric surfactant, wherein the anionic surfactant is 50% or more of surfactants, 0.5 to 3% caprylic acid, and an additional organic acid having a pKa of 4.5 to 5.0, a log P greater than 1.8 and water solubility greater than 0.5 g/100 ml, wherein the organic acid is phenylpropanoic acid;
b) combining said components of (a) to form a liquid mixture having a pH 4.5 to 5.5;
c) packaging the resulting mixture in a container.

12. A composition comprising 0.5 to 3.0% by wt. caprylic acid in compositions comprising 5 to 25% anionic surfactant, 0 to 5% by wt. non-ionic surfactant and optional amphoteric surfactant, where a pH of the composition is 4.5 to 5.5, wherein the composition is configured to provide antibacterial activity against both gram positive and gram negative bacteria; wherein there is additionally present an organic acid having pKa of 4.5 to 5.0, a log P greater than 1.8 and water solubility greater than 0.5 g/100 ml, wherein the organic acid is phenylpropanoic acid.

13. The liquid composition according to claim 1, wherein the pH is 4.5-5.1.

14. The process according to claim 11, wherein the non-ionic surfactant is present in an amount of 0.5 to 4% by wt.

\* \* \* \* \*